US008939965B2

(12) United States Patent
Liesfeld et al.

(10) Patent No.: US 8,939,965 B2
(45) Date of Patent: Jan. 27, 2015

(54) OPHTHALMIC APPARATUS AND METHOD OF OPERATING THE SAME

(75) Inventors: Ben Liesfeld, Potsdam (DE); Ulrike Weber, Potsdam (DE); Winfried Teiwes, Kleinmachnow (DE); Derk Weidauer, Kleinmachnow (DE); Kay-Uwe Amthor, Potsdam (DE); Stephan Kirsch, Birkenwerder (DE)

(73) Assignee: OD-OS GmbH, Teltow (DE)

( * ) Notice: Subject to any disclaimer, the term of this patent is extended or adjusted under 35 U.S.C. 154(b) by 327 days.

(21) Appl. No.: 12/893,678

(22) Filed: Sep. 29, 2010

(65) Prior Publication Data

US 2011/0077625 A1 Mar. 31, 2011

Related U.S. Application Data (60) Provisional application No. 61/246,763, filed on Sep. 29, 2009.

(51) Int. Cl.
*A61F 9/008* (2006.01)
*A61B 3/14* (2006.01)
*A61B 3/00* (2006.01)

(52) U.S. Cl.
CPC ............... *A61B 3/14* (2013.01); *A61B 3/0033* (2013.01); *A61B 3/0058* (2013.01); *A61B 3/0075* (2013.01); *A61F 9/008* (2013.01)
USPC .............................................. 606/4; 351/206

(58) Field of Classification Search
CPC ...... A61B 3/0033; A61B 3/0075; A61B 3/14; A61B 3/58; A61F 9/008
See application file for complete search history.

(56) References Cited

U.S. PATENT DOCUMENTS

| 5,406,076 A | * | 4/1995 | Mimura et al. | 250/229 |
| 6,547,782 B1 | * | 4/2003 | Taylor | 606/14 |
| 7,393,349 B2 | | 7/2008 | Abe et al. | |
| 2004/0044333 A1 | * | 3/2004 | Sugiura | 606/4 |
| 2004/0059321 A1 | * | 3/2004 | Knopp et al. | 606/10 |
| 2007/0073905 A1 | * | 3/2007 | Cynthia et al. | 710/1 |
| 2007/0080003 A1 | * | 4/2007 | Koerlin et al. | 180/65.1 |
| 2009/0195750 A1 | * | 8/2009 | Isogai et al. | 351/208 |

FOREIGN PATENT DOCUMENTS

JP 10091263 A * 4/1998
WO WO2008003788 A2 1/2008

OTHER PUBLICATIONS

Tom Zeller Jr., "A Great Idea That's All in the Wrist", New York Times (nytimes.com), Jun. 5, 2005.*

* cited by examiner

*Primary Examiner* — Gary Jackson
*Assistant Examiner* — Scott T. Luan
(74) *Attorney, Agent, or Firm* — Faegre Baker Daniels LLP (57) ABSTRACT

An ophthalmic apparatus including an observation system configured for displaying a moving image of a patient's eye, an optical system for directing an illumination beam into the patient's eye and for directing an observation beam from the patient's eye into the observation system, a control system configured for controlling the optical system, and a control stick for inputting control signals into the control system including an auxiliary control element being provided on the control stick for inputting auxiliary control signals into the control system, wherein the control system is configured for controlling a display mode of displaying the moving image of the observation system according to the auxiliary control signals. The invention further relates to a method of operating said ophthalmic apparatus.

28 Claims, 5 Drawing Sheets

OPHTHALMIC APPARATUS AND METHOD OF OPERATING THE SAME

CROSS-REFERENCE TO RELATED APPLICATION

This application claims the benefit under 35 U.S.C. §119 to U.S. Provisional Application No. 61/246,763, filed Sep. 29, 2009, entitled "OPHTHALMIC APPARATUS—CONTROL ELEMENT," which is herein incorporated by reference in its entirety.

The present invention relates to an ophthalmic apparatus for observing a patient's eye, in particular for observing a real-time moving picture of a posterior part of the patient's eye, the ophthalmic apparatus including a control stick for operating the ophthalmic apparatus. The invention further relates to a method of operating said ophthalmic apparatus.

Modern ophthalmic instruments for observing and treating a patient's eye often provide an abundance of complex functions for improving the acquisition of diagnostic data or for facilitating eye surgical treatments such as photocoagulation of a posterior part of an eye. To the degree that such functions are added to an ophthalmic apparatus the workflow of an operator becomes more difficult which in turn degrades usability.

In most cases therefore, during a diagnostic or treatment session the operator of such an instrument has to carry out a number of task at the same time. On the one hand the operator needs to keep contact with the head of the patient directing its position and holding the eye open. On the other hand, the operator must continuously adjust the position to the ophthalmoscope with respect to the patient's eye since the patient is usually conscious and moving his head and his eye. In the case of a laser treatment of the eye, the operator also has to control a focus of a treatment laser beam. If provided by the ophthalmoscope, the operator needs to control additional imaging and planning functions as disclosed in WO 2008/003788. Performing all these tasks successfully at the same time demands a high amount of concentration as well as considerable coordinative skills.

It is therefore the object of the present invention to provide an ophthalmic apparatus, which permits a streamlined workflow and a safe simultaneous control over essential operating functions of the ophthalmoscope including display functions or treatment functions.

This object is achieved by ophthalmic apparatus of claim 1. Further embodiments of the ophthalmic apparatus according to the invention are described in the respective dependent claims.

An ophthalmic apparatus according to invention comprises an observation system configured for displaying a moving image of a patient's eye, an optical system for directing an illumination beam into the patient's eye and for directing an observation beam from the patient's eye into the observation system, a control system configured for controlling the optical system, and a control stick for inputting control signals into the control system including an auxiliary control element being provided on the control stick for inputting auxiliary control signals into the control system, wherein the control system is configured for controlling a display mode of displaying the moving image of the observation system according to the auxiliary control signals.

In the state of the art it is known to adjust a position of the optical system of the ophthalmoscope relative to the patient's eye using translational and rotational degrees of freedom of a joystick, cf. U.S. Pat. No. 7,393,349. The control stick included in the ophthalmoscope presented here also provides this functionality. In addition to that, the control stick includes at least one auxiliary control element for inputting auxiliary control signals, in order to control the display mode of displaying the moving picture of the observation system.

The observation system receives the observation beam, which is the reflection of the illumination beam reflected on a specific region of the patient's eye to be examined and therefore carries image information about this region. In order to extract this image information, the observation beam or at least a part of the observation beam is usually focussed into a focal plane conjugate to the region of the eye to be examined. Many ophthalmoscopes include a microscope to observe the image created in this focal plane directly, as described in U.S. Pat. No. 7,393,349. Alternatively or additionally, the observation system includes a light sensitive sensor and an image processor unit, wherein the optical system is set up for focussing at least a part of the observation beam onto the sensor. The image processor unit, which is either provided as a stand-alone unit or integrated into the control system, is configured for converting image signals generated by the sensor into image data in real time, in order to create a live moving image of the patient's eye. In an embodiment, the observation system further includes at least one screen or monitor for displaying the image data as a moving image.

Examples of specific image display functions for displaying the live image of the eye are described below as well as in WO 2008/003788. An essential advantage of the presented invention is that it allows the operator to control the display mode of the moving image of the patient's eye without taking his or her hand off the control stick since the respective control elements for inputting control signals for changing or adjusting the display mode are provided on the control stick. This enables the operator to adjust the position of the ophthalmic apparatus (or at least its optical system as described above) with respect to the moving patient's eye and simultaneously control the display mode of the observation system without moving his hand from the control stick. This results in a significant reduction of the coordinative demands of controlling the apparatus and thus facilitates its operation considerably, since the operator can exert control without moving his hands between different control elements and without losing focus in a complex procedure.

In an embodiment of the ophthalmic apparatus according to the invention, the observation system can be operated in an overlay display mode. In this mode the observation system is configured for displaying at least one reference image of the patient's eye being overlaid onto the moving image. To this end, the observation system, more precisely the image processor unit of the observation system, is configured for performing an image registration of the at least one reference image of the patient's eye and the moving image of the patient's eye in real time by transforming the at least one reference image and/or the moving image into a reference coordinate system, wherein the reference coordinate system is either a fixed coordinate system or a moving object coordinate system which is tracking motions of the eye.

The at least one reference image is either an image taken during the session with the same apparatus or an image loaded into the apparatus. The reference image may be an IR image, a 2D colour image, a 3D topographic image, an angiography or any other type of image of the patient's eye. Such an image overlay helps viewing and highlighting structures within the eye only visible within one of the above representations. In a further embodiment of the invention, the image processor unit is configured for subtracting two registered images for representing differences between the respective images. This is particularly advantageous for visualizing the effect a laser pulse applied onto tissue within the eye. The image registration helps to align the at least one reference picture with the moving picture of the eye and may be implemented according to an intensity-based or a feature-based algorithm.

In the overlay mode the operator can view different representations of the eye at the time enhancing the information content and consequently the diagnostic value of the live image drastically.

In the case that the above mentioned reference coordinate system is a fixed coordinate system, the overlay display mode additionally results in an advantageous image stabilisation of the live image helping the operator tracking a particular area of the patient's eye.

The usability of the ophthalmic apparatus can be further improved according to an embodiment of the invention, wherein the control system is configured for activating and deactivating the overlay display mode, for changing an opacity of the at least one reference image being overlaid onto the moving image, or for selecting the at least one reference image among a selection of reference images according to the auxiliary control signals input into the control system. The advantage of this embodiment is that the operator can merge additional information into the moving picture during a session without moving his hands or losing his focus. This embodiment allows the operator to swiftly navigate through different representations of the eye and to select a representation including information being of importance at a particular stage of a diagnostic or treatment session.

In an embodiment of the ophthalmic apparatus according to the invention, the observation system can be operated in a marker display mode, wherein the observation system is configured for superimposing at least one marker symbol onto the moving image of the patient's eye for marking at least one area within the moving image. To this end, the marker symbols are defined in a fixed reference coordinate system and the observation system is further configured for mapping the moving image into the fixed reference coordinate system by image registration techniques. This coordinate transformation of the live image into a fixed coordinate system compensates for motions of the patient's eye, which stabilizes the live image of the patient's eye and by that helps the operator to safely mark areas within the patient's eye.

In an alternative embodiment, the coordinates of the marker symbols are transformed in real-time into a moving object coordinate system tracking the motions of the patient's eye. In this case, motions of the patient's eye are visible with the marker symbols following these motions. In this way the operator can directly observe the motion of the patient's eye and e.g. correct the position of the instrument with respect to the patient.

In both ways, the areas marked by the marker symbols always refer to the same area on the eye. In this way the marked areas can easily be tracked by the observer throughout a session, particularly a treatment session, enabling the operator to observe an effect of an application of a treatment beam onto tissue within the marked area.

In a further embodiment of the ophthalmic apparatus according to the invention, the control system is configured for activating and deactivating the marker display mode, for selecting an opacity, a colour or a functionality of the at least one marker symbol according to the auxiliary control signals input into the control system. This embodiment allows the operator to comfortably and quickly control the visibility, the representation or the functionality of the marker symbols using the auxiliary control elements provided on the control stick without taking his or her hands off the control stick, which improves significantly the usability of these marker symbols. Special examples for specific functionalities of the marker symbols are given below.

In a further development of the ophthalmic apparatus according to the invention, the observation system is configured for defining, positioning, or selecting at least one marker symbol marking at least one area within a reference image of the patient's eye according to the auxiliary control signals input into the control system. Preferably a position of the at least one marker symbol is defined within a reference coordinate system.

To the end of overlaying the marker symbols defined on a reference image onto the moving image of the patient's eye, the respective reference picture is overlaid onto the moving picture. In this way, the marker display is a further development of the overlay mode described above with additional marker functions.

The marker display function allows the operator to easily define, position, or select said at least one marker symbol without taking his or her hands off the control stick. Such operations are advantageous, for instance, for documenting effects of a treatment laser treatment on specific treatment points. A further important application of marker symbols is during a planning phase before applying a laser treatment to the patient's eye, wherein the marker symbols are used to define areas where a laser pulse should be applied. The marker symbols can also be used to identify areas, where an application of a laser pulse must be avoided.

A further development of the ophthalmic apparatus according to the invention comprises a laser system for a laser treatment of the patient's eye, wherein the control system is configured for controlling the laser system, preferably according to the auxiliary control signals input into the control system.

In a preferred embodiment of this development, the control system is configured to set laser parameters including a power of a laser beam generated by the laser system, a pulse duration, a position of a focal plane, or spot size of said laser beam according to the auxiliary control signals input into the control systems via the auxiliary control elements placed on the control stick. This embodiment has the advantage that the operator can control said parameters easily without taking his hand off the control stick, which significantly simplifies the usability of the laser during a laser treatment session, since the operator does not have to take his hand off the control stick or the patient's head in order to operate a separate control panel. This helps to prevent erroneous operations by the surgeon which could have harmful consequence, for instance when an energetic laser pulse is applied onto the macula of the patient's eye.

In an embodiment of the ophthalmic apparatus according to the invention, which includes the laser system, the observation system is operated in a parameter display mode, wherein the observation system is configured for displaying at least one laser parameter of the laser system, preferably within the moving image. This allows the operator to keep his view directed onto the observation system, or in the preferred version, wherein the said parameters are displayed on the live image, preferably within a boundary region of the live picture, onto the live image itself.

In a further development of the above embodiment of the ophthalmic apparatus according to the invention the control system is configured for activating and deactivating the parameter display mode, for adjusting an opacity or for selecting at least one laser parameter from a selection of laser parameters according to the auxiliary control signals input into the control system, which helps the operator to quickly and safely control the display of the at least laser parameters, without taking his hand off the control stick and losing his focus during a laser treatment session.

In a preferred embodiment of the ophthalmic apparatus according to the invention including a laser system, the laser system comprises a laser steering device for steering a laser beam of the laser system, wherein the control system is configured for controlling the laser steering device according to the auxiliary signals. In particular, this enables a surgeon to carry out a laser treatment by manually steering a laser beam generated by the laser system towards treatment areas within the patient's eye. Due to the integration of the auxiliary control elements on the control element the steering of the laser can be carried out without taking the hand off the control stick. Hence it is possible to control both a direction of the laser beam and the alignment of the optical system with the patient's eye at the same time.

The laser steering device may be integrated into the optical system and may be realized as at least one motorized mirror. Such a laser steering device allows steering the laser beam generated by the laser system without moving the optical system as a whole. A visible laser spot created by the laser beam on a surface of the patient's eye, preferably a laser spot of an aiming laser beam with a reduced power not affecting the eye, is steerable via the steering device within a field of view visible on the live image of the patient's eye. This laser spot is observable for the surgeon carrying out the treatment through the observation system on the live image and can be steered towards treating spots.

In a further embodiment of the ophthalmic apparatus according to the invention including the laser system, the control system is configured for providing a target assistance function, preferably by performing a real-time mapping of coordinates of a treatment area defined within a reference image with a fixed coordinate system into an object related moving coordinate system, which is tracking motions of the patient's eye. By that, the target assistance function corrects a direction of the laser beam for sudden eye movements. This target assistance function is advantageous in particular in combination with a manual steering of the laser beam in the overlay display mode defined above: On the one hand the live image is stabilized due to the transformation of the live image into the fixed coordinate system. On the other hand, the position of a treatment laser spot is being adjusted in such a way that the laser spot always remains on a predefined target point within the patient's eye.

In a further development of the invention the control system is configured for activating or deactivating the target assistance function according to the auxiliary signals, which helps the surgeon to switch the target assistance function on or off anytime during a treatment session without taking his or her hand off the control stick.

In a further development of the ophthalmic apparatus according to the invention the control system is configured for steering the laser beam towards the at least one area within the patient's eye marked by the at least one marker symbol. Preferably, the control system is configured for subsequently steering the laser beam onto a series of areas marked by a series of markers symbols automatically or upon reception of an auxiliary signal. By this means, a process of laser treatment of the patient's eye is partly automated which releases the surgeon from manually steering the laser beam during the treatment phase. By entering a discrete trigger signal through an auxiliary control element, the laser is steered through a series of treatment areas predefined during a planning session.

In a further development of the ophthalmic apparatus according to the invention the control system is configured performing a diagnostic measurement triggered by an auxiliary signal input into the control system. By this means, the operator can trigger a predefined diagnostic measurement routine at any time during a diagnostic or treatment session without taking his or her hand off the control stick.

In a further development of the ophthalmic apparatus according to the invention at least on auxiliary control element on the control stick is provided by a trackball. A trackball, preferably disposed in a position accessible for a thumb of an operator grasping the control stick, is suitable for inputting a 2D directional control signals into the control system, wherein the 2D directional control signal defines a direction in a two dimensional space. By rolling the trackball, preferably with the thumb of the hand grasping the control stick, a continuous series of such 2D directional control signals is entered defining a path in the two dimensional reference coordinate system, the length of which depending on a total rolling angle of the trackball. The trackball is therefore very convenient for entering a two dimensional translational vector with a defined length and direction necessary for controlling several of the functions described above, in particular for positioning or selecting marker symbols in a reference image and for steering the laser beam within a live or reference image of the patient's eye. Providing a translational vector relative to a momentary position is superior to providing an absolute vector referenced to an absolute origin as in the case of a potentiometer since this greatly facilitates the implementation of a target assistance function. The reason for that is that target assistance functions generally refer to momentary positions and not to absolute positions.

A further advantage of a trackball is that its response characteristics can be tuned for an improved operational ease by adjusting its response on a rotational velocity and a rotational acceleration. In a further development of the development of the ophthalmic apparatus according to the invention, the trackball is configured such that a quick and sudden rotation of the trackball about a given angle result in a longer two dimensional translational vector (e.g. for steering the laser beam or positioning a marker symbol) than a slow and smooth rotation about the same angle. In such a way two very different requirements on the steering of the treatment laser focus can be fulfilled which cannot be addressed simultaneously in the state of the art: Providing the capability to move the laser focus fast across the field of view to apply a large number of laser pulses to a large area of the fundus, which may be larger than a current field of view provided by the live image, and concurrently providing the capability to position the laser focus in minute steps very precisely. The latter is especially important applying laser pulses in the vicinity or inside of highly sensitive areas of the fundus.

In an alternative embodiment the said auxiliary control element is given by a rotary switch, an additional control stick, a 2D rocker switch, a 2D toggle switch, a touch pad, or an optical pad, which are suitable for inputting 2D directional control signals for steering a laser beam or positioning a marker symbol in a live or reference picture.

In an Ophthalmic apparatus according to one of the previous claims, characterized in that at least one further auxiliary control element is provided by a scroll wheel, which is in particular suitable for inputting laser parameters including a power of a laser beam generated by the laser system, a pulse duration, a position of a focal plane, or spot size. In alternative embodiments of the invention the said control element is provided by a rotary switch, an additional control stick, a rocker switch, or a toggle switch.

Preferably at least one of the auxiliary control elements also provides a push button function. In an embodiment of the invention, the respective control element is configured to change its input mode upon an operation of its push button function. Preferably, said at least on control element is configured to change its input mode upon a double click operation of its push button function, whereas a single click operation corresponds to a different auxiliary control signal, for instance triggering a laser beam pulse, taking a reference image of the patient's eye, or performing a diagnostic measurement.

In a further development of the ophthalmic apparatus according to the invention the control stick is provided with a illumination system configured for illuminating at least one of the at least one auxiliary control element on the control stick indicating input modes of the respective auxiliary control element, preferably each of the at least one auxiliary control element provided on the control stick is included into this illumination system. In this way, the operator always has control over the current input modes of the at least one auxiliary control element on the control stick, which helps prevent erroneous operations.

In a further development of the ophthalmic apparatus according to the invention at least one of the at least one control element on the control stick is disposed in a position accessible for a thumb of an operator grasping the control stick, preferably those auxiliary control elements configured for inputting 2D directional control signals, for instance for steering the laser beam or positioning marker symbols on a live or reference picture of the patient's eye. Since the thumb is the most flexible finger on a hand, it is most convenient to use the thumb for performing such complex operations.

The invention further provides a method of operating an ophthalmic apparatus according to the invention, wherein an operator is grasping the control stick with one hand and operates the at least one auxiliary control element with a finger on said hand. In this way, the operator can keep this hand on the control stick during a session controlling the most important functions of the apparatus by moving the joystick or by operating the at least one auxiliary control element on the joystick with one of his or her fingers.

One example of an ophthalmic apparatus according to the invention is now specified. They are shown in.

Here, as in the following, the same or reference numerals are used for the same or similar components, so that under circumstances, there is no repeated description of these.

Figure 1:
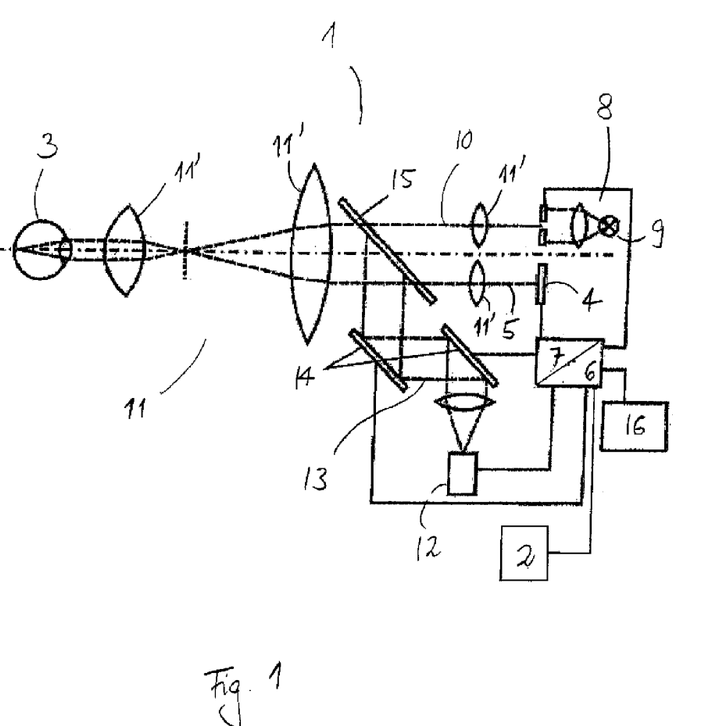
FIG. 1: a schematic representation of an ophthalmic apparatus according to the invention.

FIG. 1 shows a schematic representation of an ophthalmic apparatus (1) according to the invention, which comprises an observation system (2) including a screen for displaying a moving image of a patient's eye (3). The observations system further comprises a light sensitive sensor (4) for detecting an observation beam (5) being reflected at the eye (3) and an image processor unit (6), which is integrated into a control system (7) of the ophthalmic apparatus (1). An illumination system (8) comprises a light source (9) for creating an illumination beam (10), which is directed into the patient's eye (3) by an optical system (11) comprising condensing lenses (11') for directing the illumination beam (10) into the patient's eye (3) and the observation beam (5) onto the sensor (4). The ophthalmic apparatus (1) further comprises a laser system (12) for creating a laser beam (13) and a laser steering device (14) for steering the laser beam (13). The optical system (11) includes a beam splitter (15) as an optical coupling device for coupling the laser beam (13) into the optical system (11). Finally, the ophthalmic apparatus (1) comprises a control stick (16) for inputting control signals into the control system (7), which is further described below.

Figure 2:
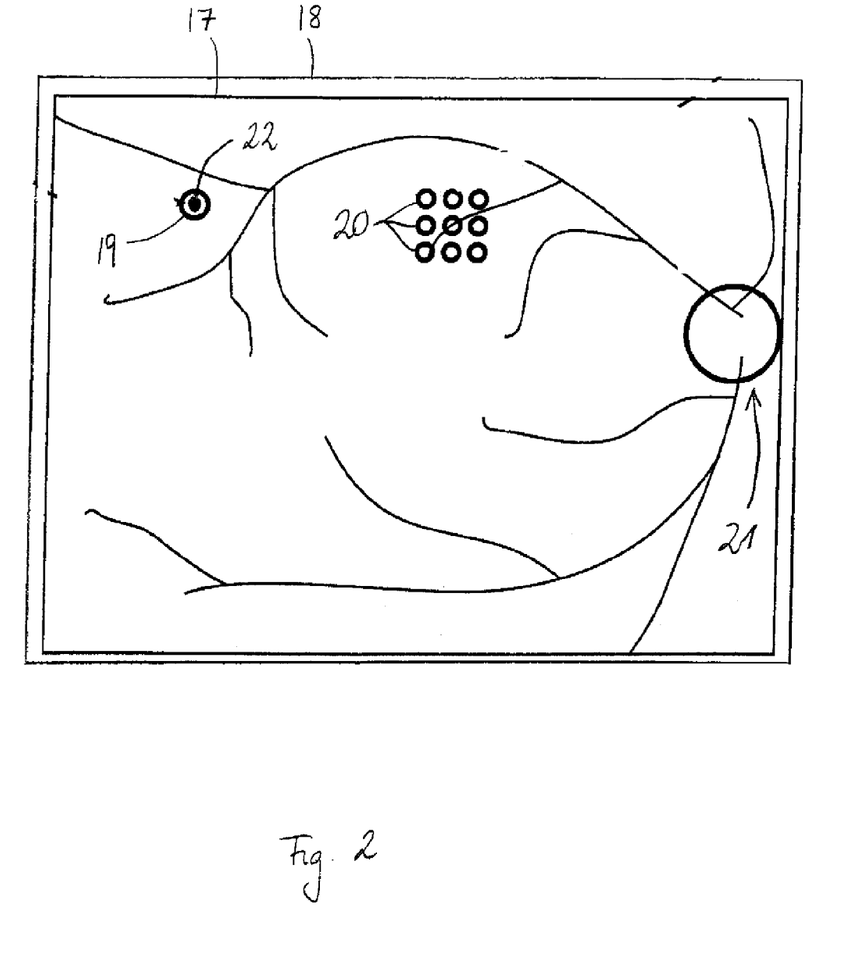
FIG. 2: a schematic representation of an exemplary moving image of a patient's eye created and displayed by an ophthalmic apparatus according to the invention

FIG. 2 shows a schematic representation of an exemplary moving image (17) of a patient's eye (3) created and displayed by an ophthalmic apparatus (1) according to the invention, for instance by an embodiment of the invention according to FIG. 1. The image is displayed in a marker display mode, wherein the moving image and a reference image (18) are registered and overlaid onto each other in real time by an image processor unit (6) of the ophthalmic apparatus (1). The reference image (18) contains marker symbols (19, 20, 21), which are defined within a reference coordinate system fixed to the reference image (17). The moving image is transformed into the reference coordinate system by registration so that movements of the eye (3) of the patient are compensated. (In an alternative embodiment the reference image and the marker symbols are transformed into a moving object coordinate system tracking motions of the patient's eye.) The first marker symbol (17) indicates a first treatment area of the patient's eye. A laser beam (13) is automatically steered onto a centre of the first marker symbol (17) by a laser steering device (14) of the ophthalmic apparatus (1) creating a laser spot (22). The laser steering device (14) is controlled by a control system, which is configured for providing a target assistance function compensating for motions of the eye during a laser treatment as described above. The laser system is further configured for creating a treatment laser beam and an aiming laser beam, the latter having a reduced power without any therapeutic effect on the patient eye. The aiming beam is coaxial with the treatment beam and serves for controlling an orientation of the laser system relative to the patient's eye.

A set further marker symbols (20) indicate further laser treatment spots, whereas the marker symbol (21) indicates an exclusion area of the patient's eye, where no laser treatment must be applied, for instance a macula of the patient's eye. Preferably, marker symbols indicating treatment zones and marker symbols indicating exclusion zones differ in the colours to be easily distinguishable by the surgeon. The control system is configured to subsequently steer the beam (13) towards the treatment areas marked by the marker symbols (20) and (21) upon an auxiliary control signal input entered via an auxiliary control element on the control stick (22) of the ophthalmic apparatus (1), which will be described below in greater detail.

Figure 3:
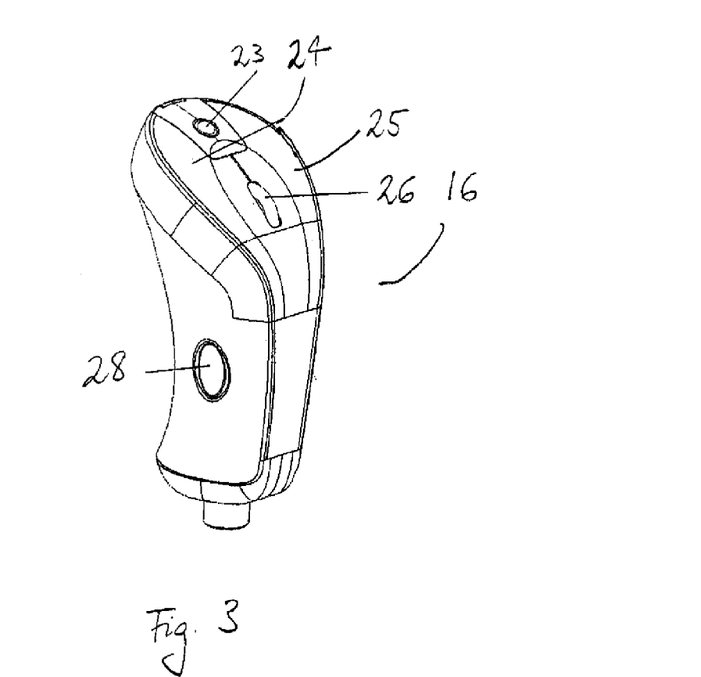
FIG. 3: a control stick of an ophthalmic apparatus according to the invention.

FIG. 2 shows a schematic representation in side view of a control stick (16) of an ophthalmic apparatus (1) according to the invention, for instance by an embodiment of the invention according to FIG. 1 or FIG. 2. The control stick (joystick) (1) is designed ergonomically to fit to either a right or a left hand of a majority of the human population. The control stick (16) is provided with a number of auxiliary control elements (23, 24, 25, 26, 27, 28) for inputting auxiliary control signal, which will be explained in detail in the following. The control elements are positioned symmetrically to a vertical plane to facilitate right and left hand use. In order to transparently display the input modes of these auxiliary control elements (23, 24, 25, 26, 27, 28) the control stick (16) is provided with an illumination system for illuminating each of the auxiliary control elements (23, 24, 25, 26, 27, 28) according to an input mode of the respective auxiliary control element (23, 24, 25, 26, 27, 28).

Auxiliary control element (23) is a trackball. Rotation of the trackball (23) creates an accurate positioning signal for a laser spot (22) of a laser beam (13) generated by a laser system of the ophthalmic apparatus (1) within a field of view shown on a screen of an observation system (2) of the ophthalmic apparatus (1), for instance a moving image of a patient's eye (3), cf. FIGS. 1 and 2.

The trackball (23) additionally provides a push button function. In an input mode of the trackball (23) suitable during a laser treatment of the patient's eye, the surgeon pushes the trackball (23) configured to select a marker symbol (19, 20) positioned on a reference image (17) overlaid onto a moving picture (18) of the patient eye (3), cf. FIG. 2. By pressing this push button in this input mode of the trackball (23), the operator switches from one planned treatment location to a next planned treatment location marked by marker symbols (19, 20). The laser system comprises a laser steering device (14) controlled by a control system (7) of the ophthalmic apparatus (1) for steering the laser beam (13). Upon reception of the push button signal, a treatment laser spot (22) is automatically targeted onto the desired treatment area marked by a marker symbol (19, 20) by the control system (7). A treatment laser pulse is triggered for instance by operating a foot pedal.

In a further input mode of the trackball (23), an image acquisition mode, the trackball (23) is configured for triggering an image acquisition upon operating the push button function of the trackball (23). Hence in this image acquisition mode, the operator pushes the trackball (23) whenever a snapshot of the patient's eye (3) needs to be taken, for instance for documenting a treatment session.

The said apparatus (1) also provides modes of operation other than treatment mode namely a diagnostic mode. In the diagnostic mode the trackball is used in an input mode configured for defining marker symbols (19, 20) and controlling positions of such marker symbols (19, 20) on a reference image (18) displayed by the observation system (2). Hence, the surgeon defines and positions these marker symbols (19, 20) in similar way as operating a computer mouse. In particular planning of the treatment areas requires accurate positioning of graphical elements, such as the marker symbols (19, 20) on a screen of the observation system (2). This is performed more easily with the trackball (23) than with a stylus on the touchsensitive screen or with a computer mouse given the restricted spatial conditions in a doctor's practice. A further advantage of the trackball (23) placed on the control stick (16) is that the surgeon can always keep his hand on the control stick during the treatment mode as well as during the diagnostic or planning mode. Pressing the trackball in diagnostic mode makes the apparatus perform a diagnostic measurement.

The trackball (23) is disposed in a position accessible for a thumb of an operator grasping the control stick. In this way, the surgeon easily operates the trackball (23) with his thumb by rolling the trackball in any direction in order to input 2D directional control signals or by pushing the trackball entering a simple trigger signal into the control system (7).

Auxiliary control element (24) disposed on the left hand side of the trackball (23) is configured for controlling a visibility of graphical indicators such as marker symbols on the live moving image of the ophthalmoscope (1), which were defined in a previous planning step. An auxiliary control element (24) on the right hand side (25) of the trackball (23) is configured to control the visibility of still reference images (18) which are overlaid onto the live moving image (17). So by operating the auxiliary control elements (23, 24) the operator can switch on and off an overlay display mode and a marker display mode of the observation system (2), which are described above.

In the example presented here, a functionality of the marker symbols (19, 20, 21) is coupled to their visibility. Deactivating the display of the marker symbols (19, 20, 21) for the treatment areas or for the exclusion areas (21) also disables their function. The operator is therefore capable of quickly interfering with automated processes, such as the steering of the laser beam (13) to predefined treatment locations, without taking his hand off the joystick (16). The switches (23, 24) are configured such that pushing them a number of times in quick succession produces different results. In particular, pressing the left switch (23) once disables the automated control function related to the markers symbols (19, 20, 21), such as indicating areas as treatment areas (19, 20) or exclusion areas (21). At the same time, the colors of these marker symbols (19, 20, 21) are changed. Pressing the left switch (24) twice in quick succession also disables the display of these marker symbols (19, 20, 21).

Pressing the right switch (24) switches an opacity of the reference image overlaid onto the moving image between a number of preconfigured values, including a user preferred setting of the opacity, 50% of that value, 100% and 0%, the latter value corresponding to switching the overlay mode off.

A further auxiliary control element (26) disposed just below the trackball (23) is provided as a scroll wheel, which is configured to be operable in two different input modes, wherein in the first input mode the control wheel is configured for controlling a focus of an illumination beam (10) and in a second input modus the scroll wheel is configured for controlling a focus of the laser beam (13), cf. FIG. 1. These two input modes can be activated and selected by operating a push button function of the scroll wheel (26). In the first input mode focus indicators of the ophthalmoscope (1) are activated and rotating the scroll wheel adjusts the focal plane of the ophthalmoscope (1) according to refractive properties of the patient's eye (1). In the second input mode a focal plane of the treatment laser is controlled, preferably with respect to an imaging beam path.

Figure 4:
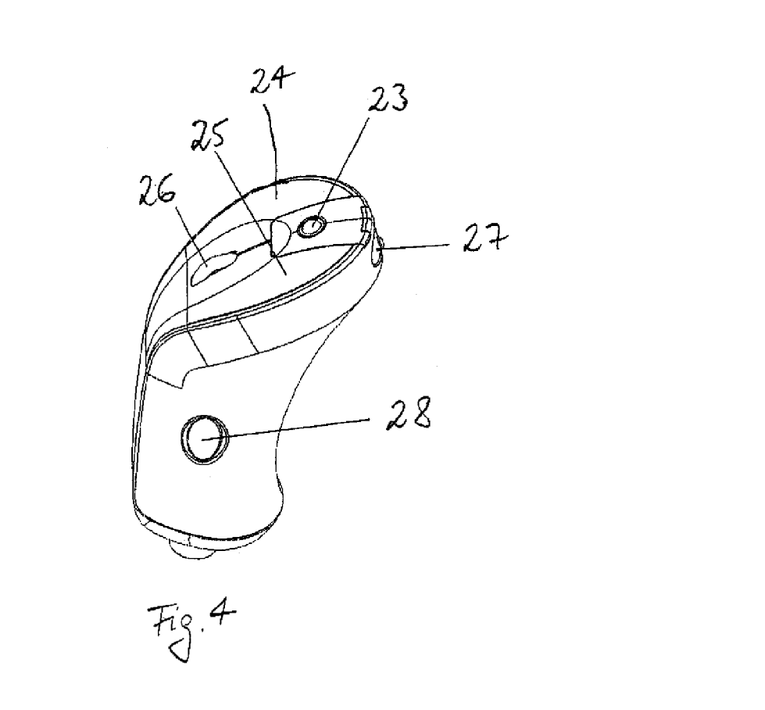
FIG. 4: a control stick of an ophthalmic apparatus according to the invention.

In FIG. 4 the exemplary control stick (16) described above and shown in FIG. 3 is schematically represented in an oblique view from above. An auxiliary control element (27) is provided on a front side of the control stick opposite to operator. In a diagnostic or treatment session the operator operates this auxiliary control element (27) with a forefinger of his hand grasping the control stick (16).

This auxiliary control element (27) has a push button function being configured for turning on and of automated processes of the ophthalmic apparatus (1) such as tracking functions or target assistance functions described above.

Two further auxiliary control elements (28) are push buttons positioned symmetrically on either side of the joystick (16). They are configured for controlling the engagement or release of a brake restricting mechanical degrees of freedom for positioning the apparatus (1) mechanically relatively to the patient's eye (3). In the present embodiment, the brake is configured for fixing a distance between the apparatus (1) and the patient's eye and for only allowing for rotational degrees of freedom of the apparatus (1) around the pupil of the patient's eye. In this case, the instrument is aligned to the patient's eye first, then its distance to the eye (3) is fixed by engaging said brake via control element (28). Finally, the apparatus (1) is rotated around the pupil of the eye (3) while the center of rotation is invariably located in the pupil of the eye.

As known from the state of the art, tilting the joystick (16) results in a translational horizontal movement of the entire apparatus (1). The joystick can be rotated along its longitudinal axis. The angle of this rotation is detected and translated into a vertical movement of the apparatus (1). By this means, the surgeon can keep the apparatus (1) adjusted in a correct working position relative to the patient's eye, without taking his or her hand off the control stick (16). In a further embodiment of the invention, the operator may not sit at the instrument aligned with the optical axis of the instrument but rather at a side of the instrument facilitating access to the patient's head. In this case the equilibrial position of the joystick may be adjusted around a longitudinal axis of the control stick in such a way that a symmetry plane of the joystick is aligned with the position of the operator.

Figure 5:
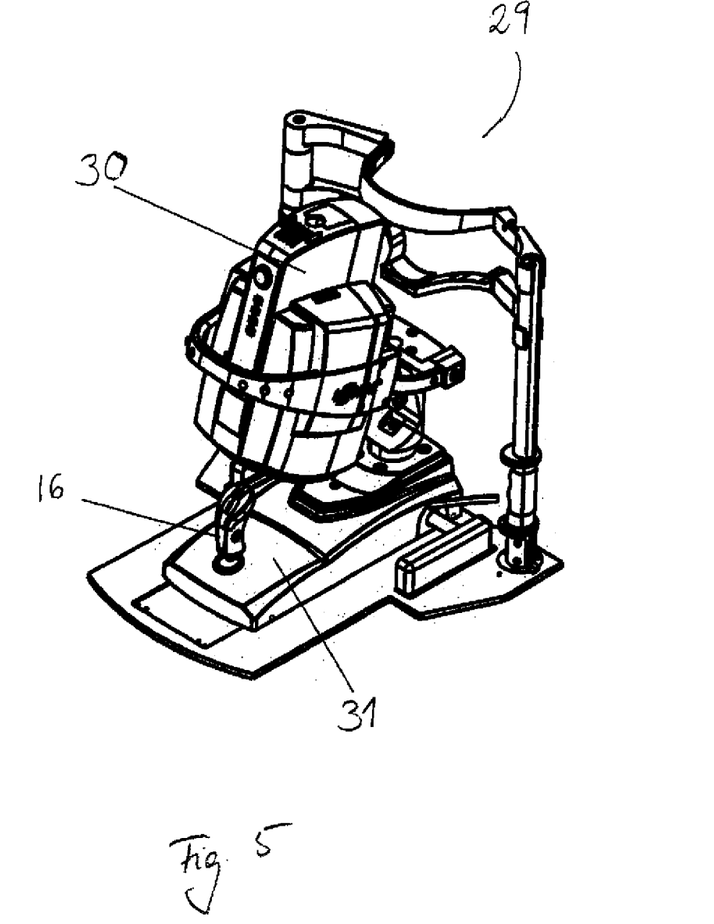
FIG. 5: a schematic representation of a main unit of an ophthalmic apparatus according to the invention.

FIG. 5 shows a schematic representation of a main unit (29) of an exemplary embodiment of an ophthalmic apparatus (1) according to the invention. It comprises an optical unit (30) containing the optical system (11) and a laser system (12), and an instrument base (31) with a control stick (16).

Figure 6:
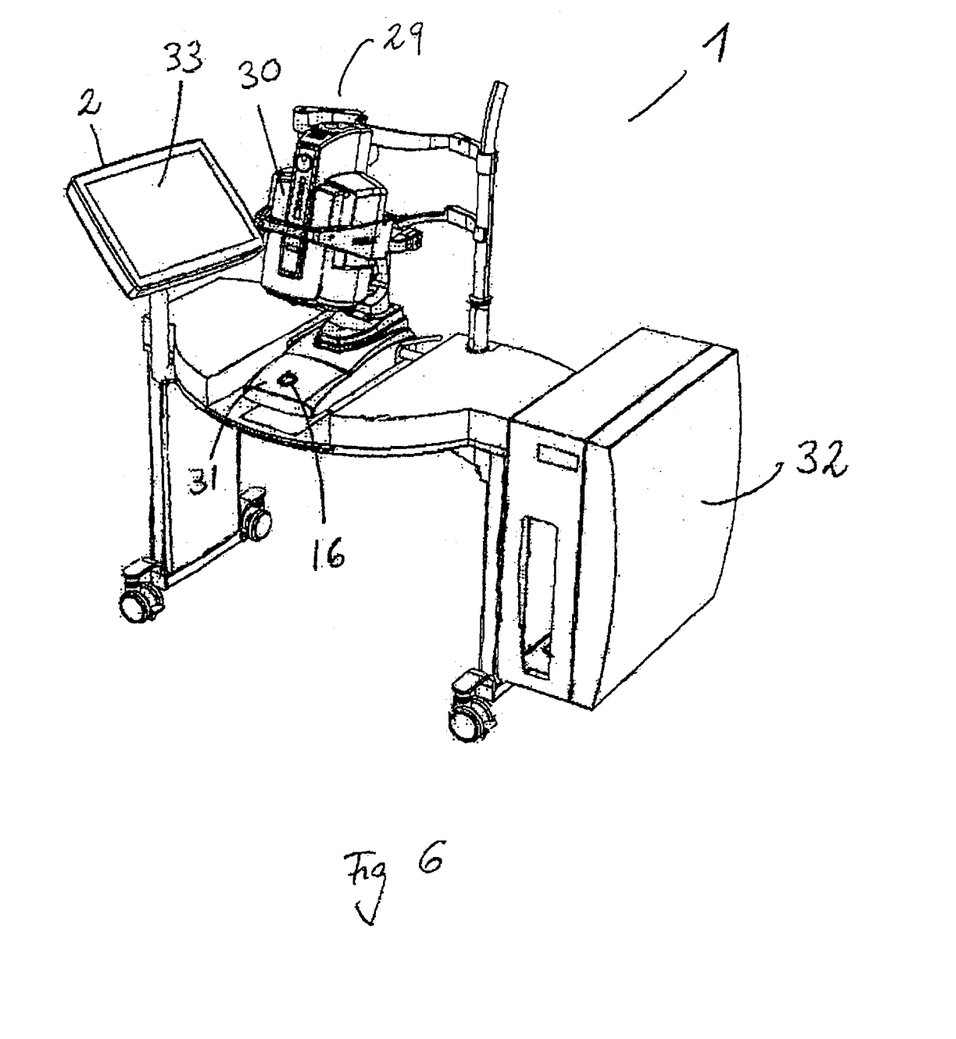
FIG. 6: a schematic representation of an ophthalmic apparatus according to the invention.

In FIG. 6 shows a schematic representation of an exemplary embodiment of an ophthalmic apparatus according to the invention. It comprises an optical unit (30) containing the optical system (11) and a laser system (12), and an instrument base (31) with a control stick (16), an observation system (2) with a screen (2') and a image processor unit (6) integrated into a control system (7), which in this case is provided by a PC.

The invention claimed is:

1. An ophthalmic apparatus comprising:
an observation system configured for displaying a moving image of a patient's eye;
an optical system for directing an illumination beam into the patient's eye and for directing an observation beam from the patient's eye into the observation system;
a control system configured for controlling the optical system; and
a control stick for inputting control signal into the control system, wherein the control stick, the control system and the optical system are operatively connected and configured for synchronous real-time conversion of motions of the control stick into motions of the optical system to enable the operator to compensate for motions of the patient's eye such that an alignment of the optical system with the patient's eye is sustained, the control stick including an auxiliary control element being provided on the control stick for inputting auxiliary control signals into the control system;
wherein the control system is configured for controlling a display mode of displaying the moving image of the observation system according to the auxiliary control signals,
further wherein the auxiliary control element comprises a 2D auxiliary control element configured for inputting 2D directional auxiliary control signals into the control system,
wherein the ophthalmic apparatus includes a laser system for a laser treatment of the patient's eye, wherein the control system is configured for controlling the laser system according to the auxiliary control signals input into the control system and the laser system includes a laser steering device for steering a laser beam of the laser system, wherein, to enable the operator to manually steer the laser beam towards treatment areas within the patient's eye by manually operating the 2D auxiliary control element, the control system and the laser steering device are configured for synchronous real-time conversion of motions of the 2D auxiliary control element into motions of the laser steering device.

2. An ophthalmic apparatus according to claim 1, wherein the 2D auxiliary control element on the control stick is provided by a trackball, an additional control stick, a touch pad, an optical pad, a rocker switch, or a toggle switch.

3. An ophthalmic apparatus according to claim 1, wherein the 2D auxiliary control element on the control stick is disposed in a position accessible for a thumb of an operator grasping the control stick.

4. An ophthalmic apparatus according to claim 1, wherein the auxiliary control element also provides a push button function.

5. An ophthalmic apparatus according to claim 4, wherein the auxiliary control element is configured to change an input mode of the auxiliary control element upon an operation of its push button function.

6. An ophthalmic apparatus according to claim 1, wherein the control stick is provided with an illumination system configured for illuminating the 2D auxiliary control element indicating an input mode of the auxiliary control element.

7. An ophthalmic apparatus according to claim 1, wherein in an overlay display mode the observation system is configured for displaying at least one reference image of the patient's eye being overlaid onto the moving image.

8. An ophthalmic apparatus according to claim 7, wherein the control system is configured for activating and deactivating the overlay display mode, for changing an opacity of the at least one reference image being overlaid onto the moving image, or for selecting the at least one reference image among a selection of reference images according to the auxiliary control signals input into the control system.

9. An ophthalmic apparatus according to claim 7, wherein the observation system is configured for defining, positioning, or selecting at least one marker symbol marking at least one area within the reference image of the patient's according to the 2D directional auxiliary control signals being input into the control system during the overlay of the reference image onto the moving image of the patient's eye.

10. A method of operating an ophthalmic apparatus according to claim 9, wherein an operator is grasping the control stick with one hand and is manually conducting the motions of the control stick in response to the motions of the patient's eye to manually sustain an alignment of the optical system with the patient's eye, wherein the motions of the control stick are converted into the motions of the optical system so as to enable the operator to manually compensate for the motions of the patient's eye relative to the optical system, wherein the operator, at the same time, operates the 2D auxiliary control element with a finger on said hand to input 2D directional auxiliary control signals into the control unit, and further wherein the observation system overlays onto the moving image at least one reference image of the patient's eye, wherein, simultaneously, the operator inputs into the control system 2D directional auxiliary control signals, wherein the observation system defines, positions, or selects at least one marker symbol marking at least one area within the reference image according to the 2D directional auxiliary control signals.

11. An ophthalmic apparatus according to claim 1, wherein in a marker display mode the observation system is configured for superimposing at least one marker symbol onto the moving image of the patient's eye for marking at least one area within the moving image, wherein, for achieving a stabilization of the moving image of the patient's eye, the observation system is configured to map the moving image onto a fixed reference coordinate system, the observation system being further configured to define the position of the marker symbol in the reference coordinate system according to 2D directional auxiliary control signals being input during said stabilization of the moving image.

12. An ophthalmic apparatus according to claim 11, wherein the control system is configured for activating and deactivating the marker display mode, for selecting an opacity, a color or a functionality of the at least one marker symbol according to the auxiliary control signals input into the control system.

13. A method of operating an ophthalmic apparatus according to claim 11, wherein an operator is grasping the control stick with one hand and is manually conducting the motions of the control stick in response to the motions of the patient's eye to manually sustain an alignment of the optical system with the patient's eye, wherein the motions of the control stick are converted into the motions of the optical system so as to enable the operator to compensate for the motions of the patient's eye relative to the optical system, wherein the operator, at the same time, is operating the 2D auxiliary control element with a finger on said hand to input 2D directional auxiliary control signals into the control unit, wherein the observation system superimposes at least one marker symbol onto the moving image of the patient's eye for marking at least one area within the moving image, and further wherein the moving image of the patient's eye is stabilized by mapping the moving image onto a fixed reference coordinate system by means of the observation system, wherein, during this stabilization of the moving image, the operator enters 2D directional auxiliary control signals via the 2D auxiliary control element, wherein the observation system positions the at least one marker symbol with respect to the fixed reference coordinated system according to the entered 2D directional auxiliary control signals.

14. An ophthalmic apparatus according to claim 1, wherein in a parameter display mode the observation system is configured for displaying at least one laser parameter of the laser system.

15. An ophthalmic apparatus according to claim 14, wherein the control system is configured for activating and deactivating the parameter display mode, for adjusting an opacity of the at least one displayed parameter or for selecting at least one laser parameter from a selection of laser parameters according to the auxiliary control signals input into the control system.

16. An ophthalmic apparatus according to claim 1, wherein the control system is configured for activating or deactivating a target assistance function according to the auxiliary signals, wherein the target assistance function is configured for compensating motions of the eye during a laser treatment.

17. An ophthalmic apparatus according to claim 1, wherein the observation system is configured for defining, positioning, or selecting at least one marker symbol marking at least one area within a reference image of the patient's eye according to the 2D directional auxiliary control signals input into the control system, and wherein the control system is further configured for steering the laser beam towards the at least one area within the patient's eye marked by the at least one marker symbol.

18. An ophthalmic apparatus according to claim 1, wherein the ophthalmic apparatus is configured to perform a diagnostic measurement triggered by an auxiliary signal input into the control system.

19. A method of operating an ophthalmic apparatus according to claim 1, wherein an operator is grasping the control stick with one hand and is manually conducting motions of the control stick in response to motions of the patient's eye to sustain an alignment of the optical system with the patient's eye, wherein the motions of the control stick are converted into the motions of the optical system in synchronous real-time to allow the operator to manually compensate for the motions of the patient's eye, wherein the operator, at the same time, operates the 2D auxiliary control element with a finger on said hand to input 2D directional auxiliary control signals into the control unit.

20. The method of claim 19, wherein the motions of the optical system comprise vertical and horizontal motions of the ophthalmic apparatus or optical system relative to the patient's eye.

21. The method of claim 19, wherein the motions of the control stick comprise tilting, translating, and/or rotating the control stick to generate the control signals.

22. The method of claim 19, wherein the method further comprises:
engaging a brake of the ophthalmic apparatus with a second auxiliary control element on the control stick, wherein the brake is configured to fix a distance between the ophthalmic apparatus and the patient's eye and allow for rotational degrees of freedom of the ophthalmic apparatus around the patient's eye.

23. The method of claim 19, wherein the operator, at the same time, controls the display mode of the observation system by entering auxiliary control signals via a second auxiliary control element without moving his hand from the control stick.

24. The ophthalmic apparatus of claim 1, wherein a second auxiliary control element is configured to control an engagement or release of a brake of the ophthalmoscope, and wherein the brake is configured to fix a distance between the ophthalmic apparatus and the patient's eye and allow for rotational degrees of freedom of the ophthalmic apparatus around the patient's eye.

25. A method of operating an ophthalmic apparatus according to claim 1, wherein an operator is grasping the control stick with one hand and is manually conducting motions of the control stick in response to motions of the patient's eye to sustain an alignment of the optical system with the patient's eye, wherein the motions of the control stick are converted into the motions of the optical system in synchronous real-time to allow the operator to manually compensate for the motions of the patient's eye, wherein the operator, at the same time, operates the 2D auxiliary control element with a finger on said hand to input 2D directional auxiliary control signals into the control unit, and wherein the operator, at the same time, keeps contact with the head of the patient to direct the patient's head and/or hold the patient's eye open.

26. A method of operating an ophthalmic apparatus according to claim 1, wherein an operator is grasping the control stick with one hand and is manually conducting motions of the control stick in response to motions of the patient's eye to sustain an alignment of the optical system with the patient's eye, wherein the motions of the control stick are converted into the motions of the optical system in synchronous real-time to allow the operator to manually compensate for the motions of the patient's eye, wherein the operator, at the same time, operates the 2D auxiliary control element with a finger on said hand to input 2D directional auxiliary control signals into the control unit, and further wherein motions of the 2D auxiliary control element are converted into motions of the laser steering device in synchronous real-time so as to enable the operator to manually steer the laser beam towards treatment areas within the patient's eye by operating the 2D auxiliary control element.

27. An ophthalmic apparatus according to claim 1, wherein the real-time conversion of motions of the control stick into motions of the optical system relative to the patient's eye includes a real-time conversion of translational or tilting motions of the control stick into horizontal motions of the optical system and/or a real-time conversion of rotational motions of the control stick into vertical motions of the optical system.

28. A method of operating an ophthalmic apparatus, the apparatus including an observation system configured for displaying a moving image of a patient's eye; an optical system for directing an illumination beam into the patient's eye and for directing an observation beam from the patient's eye into the observation system; a control system configured for controlling the optical system; and a control stick for inputting control signals into the control system, a 2D auxiliary control element being provided on the control stick and configured for inputting 2D directional auxiliary control signals into the control system, the method comprising:

grasping the control stick with one hand of an operator;

manually manipulating the control stick in response to motions of the patient's eye to sustain an alignment of the optical system with the patient's eye, wherein said motions of the control stick are converted into motions of the optical system so as to enable the operator to manually compensate for the motions of the patient's eye relative to the optical system;

operating, at the same time, the 2D auxiliary control element with a finger on the one hand to input 2D directional auxiliary control signals into the control unit; and contacting the patient, at the same time and by the operator, to move the patient's head and/or hold the patient's eye open.

* * * * *